United States Patent [19]

Klaui

[11] 4,089,968

[45] May 16, 1978

[54] STABLE SOLUTIONS OF IPRONIDAZOLE

[75] Inventor: Heinrich Klaui, Riehen, Switzerland

[73] Assignee: Hoffmann-La Roche Inc., Nutley, N.J.

[21] Appl. No.: 779,977

[22] Filed: Mar. 22, 1977

[30] Foreign Application Priority Data

Apr. 5, 1976 Austria .................................. 2434/76

[51] Int. Cl.$^2$ ................... A61K 31/415; C07D 233/92
[52] U.S. Cl. ................................. 424/273 R; 548/338
[58] Field of Search ......................... 548/338; 424/273

[56] References Cited

U.S. PATENT DOCUMENTS 3,634,446  1/1972  Hoffer et al. ........................ 548/338

Primary Examiner—Richard L. Raymond
Attorney, Agent, or Firm—Samuel L. Welt; Bernard S. Leon; R. Hain Swope

[57] ABSTRACT

Solutions of ipronidazole are disclosed which have excellent stability and physiological acceptance and thereby are amenable to parenteral administration. The subject preparations utilize as the solvent for ipronidazole a mixture of water and glycerinformal.

4 Claims, No Drawings

STABLE SOLUTIONS OF IPRONIDAZOLE

BACKGROUND OF THE INVENTION

Ipronidazole, which chemically is 1-methyl-2-isopropyl-5-nitroimidazole, is a known compound. The preparation of this compound and its water-soluble salts are set out in U.S. Pat. No. 3,634,446 issued Jan. 11, 1972. Ipronidazole is highly useful in the field of veterinary medicine as it is active as an antiprotozoal and antihistomonal agent, particularly in the treatment of turkey blackhead disease or enterohepatitis. Ipronidazole is further useful in the prophylaxis and treatment of swine dysentery.

Due to the low water solubility of ipronidazole, water-soluble pharmaceutically acceptable acid addition salts thereof, preferably the hydrochloride, must be utilized when it is to be administered parenterally or in solution, e.g. in drinking water. A hinderance in the utilization of this highly active compound in solution, however, is that the shelf life of aqueous, physiologically compatible solutions of the aforementioned salts is limited by their low chemical stability. It has now been found in accordance with the present invention that aqueous solutions of free ipronidazole can be prepared which are physiologically compatible and which are not characterized by the instability demonstrated by aqueous solutions of the pharmaceutically acceptable acid addition salts thereof.

DETAILED DESCRIPTION OF THE INVENTION

In accordance with the present invention stable, physiologically compatible solutions of ipronidazole are provided wherein the solvent is part water and principally glycerinformal. Solutions of ipronidazole prepared in accordance with the present invention have been found to be very stable over extended storage and over a wide temperature range.

The glycerinformal utilized to prepare solutions of ipronidazole in accordance with the present invention is a condensation product of glycerin and formaldehyde as described in the J. of Pharmacy and Pharmacology, Vol II, p. 150 (1959). Glycerinformal is approximately a one to three mixture of 4-hydroxymethyl-1,3-dioxolane and 5-hydroxy-1,3-dioxane. Commercially available glycerinformal may contain small amounts, i.e. about 0.02% by weight, of conventional additives such as, for example, complex forming agents such as ethylenediaminetetraacetic acid or its disodium salt, antioxidants such as BHA (butylhydroxyanisole), BHT (3,5-di-tert.butyl-4-hydroxytoluene), thiodipropionic acid or alkyl esters of gallic acid such as propyl gallate or octyl gallate or the like. The presence of such additives is likewise contemplated in the solutions of the subject invention and, if required, additional amounts thereof can be added to bring their concentration in the final solution to an effective level thereby adding to the stability of the contemplated solutions.

The stable solutions of ipronidazole provided in accordance with the present invention contain, per 100 parts by volume, from about 5 to about 15 parts by weight, preferably about 10 parts by weight ipronidazole, from about 60 parts by volume to about 75 parts by volume, preferably about 70 parts by volume, glycerinformal and the remainder water. The solutions are prepared simply by dissolving the ipronidazole in the glycerinformal and adjusting to the final volume with water. Additives such as described above may be incorporated by simply dissolving them in either the glycerinformal or the water, whichever is most convenient in terms of solubility. The solutions may be sterilized, if desired, by conventional means.

The solutions provided in accordance with the present invention possess a high degree of physical and chemical stability as well as excellent physiological compatibility. They are therefore eminently suited for parenteral administration. In terms of parenteral administration, the solutions of the present invention are clearly superior to solutions prepared with similar solvents such as, for example, 1,2-propyleneglycol/ethanol or polyethyleneglycol 400/ethanol mixtures. Further, the solutions of the present invention are readily utilizable as concentrates to be added to the drinking water of the animals or fowl to be treated since they readily disperse in water with no evidence of turbidity. This property renders the subject solutions particularly advantageous from the viewpoint of practical utilization.

The following examples further illustrate the invention.

EXAMPLE 1

1.0 Gram of ipronidazole free base was dissolved in 7.0 ml of commercial glycerinformal containing 0.02% by weight BHT and 0.02% by weight disodium ethylenediaminetetraacetic acid and the solution was brought to a final volume of 10.0 ml with distilled water.

EXAMPLE 2

A solution was prepared by dissolving 10.2 g. ipronidazole in 0 ml of glycerinformal and the final volume brought to .0 ml with distilled water. The resulting clear solution was sterilized at 120° C.

EXAMPLE 3

A solution was prepared by dissolving 10.1 g. of ipronidazole in 75.0 ml of glycerinformal and the solution was brought to a total volume of 100.0 ml with distilled water.

EXAMPLE 4

A solution was prepared by dissolving 5.0 g. of ipronidazole in 60.0 ml of glycerinformal and the solution was brought to a total volume of 100.0 ml with distilled water.

EXAMPLE 5

A solution was prepared by dissolving 15.0 g. of ipronidazole in 75.0 ml of glycerinformal and the solution was brought to a total volume of 100.0 ml with distilled water.

EXAMPLE 6

One thousand grams of ipronidazole were dissolved in 7.0 liters of commercial glycerinformal containing 0.2% by weight BHT and 0.2% by weight of the disodium salt of ethylenediaminetetraacetic acid. The solution was brought to a final volume of 10.0 liters with Water for Injection filtered through a bacterial filter and filled into 100 ml ampules. The ampules were heat sterilized in an autoclave for 20 minutes at 121° C.

I claim:
1. A composition consisting essentially of a stable solution of ipronidazole in glycerinformal and water wherein each 100 parts by volume of said solution con- tains from about 5 parts by weight to about 15 parts by weight ipronidazole, from about 60 parts by volume to about 75 parts by volume glycerinformal and the remainder water.

2. A composition in accordance with claim 1 wherein said composition contains about 10 parts by weight ipronidazole.

3. A composition in accordance with claim 1 wherein said composition contains about 70 parts by volume glycerinformal.

4. A composition in accordance with claim 1 wherein said composition contains about 10 parts by weight ipronidazole, and about 70 parts by volume glycerinformal.

* * * * *